(12) United States Patent
Fraschini et al.

(10) Patent No.: US 11,977,189 B2
(45) Date of Patent: May 7, 2024

(54) METHOD AND SYSTEM FOR PROCESSING BEAMFORMED DATA PRELIMINARY CLASS

(71) Applicant: SUPERSONIC IMAGINE, Aix-en-Provence (FR)

(72) Inventors: Christophe Fraschini, Aix-en-Provence (FR); William Lambert, Marseilles (FR)

(73) Assignee: SUPERSONIC IMAGINE, Aix en Provence (FR)

( * ) Notice: Subject to any disclaimer, the term of this patent is extended or adjusted under 35 U.S.C. 154(b) by 0 days.

(21) Appl. No.: 18/064,096

(22) Filed: Dec. 9, 2022

(65) Prior Publication Data
US 2023/0184913 A1    Jun. 15, 2023

(30) Foreign Application Priority Data

Dec. 10, 2021 (EP) .................................. 21315271

(51) Int. Cl.
*G01S 7/52* (2006.01)
*A61B 8/08* (2006.01)
*G01S 15/89* (2006.01)

(52) U.S. Cl.
CPC ...... *G01S 7/52077* (2013.01); *G01S 15/8918* (2013.01); *A61B 8/5269* (2013.01)

(58) Field of Classification Search
CPC ....... A61B 8/52; A61B 8/4483; A61B 8/5269; G01S 7/52046; G01S 7/52077; G01S 7/52063; G01S 15/8915; G01S 15/8918; G16H 30/40
See application file for complete search history.

(56) References Cited

U.S. PATENT DOCUMENTS

| 2006/0173312 A1 | 8/2006 | Jackson et al. |
| 2019/0137601 A1* | 5/2019 | Driscoll ................. G01S 13/424 |
| 2020/0158844 A1* | 5/2020 | Li ............................. A61B 8/54 |
| 2023/0147070 A1* | 5/2023 | Driscoll .................... G01S 7/03 |
| | | 342/175 |
| 2023/0184913 A1* | 6/2023 | Fraschini ............ G01S 7/52063 |
| | | 367/7 |

FOREIGN PATENT DOCUMENTS

| EP | 4194893 A1 * | 6/2023 | ......... G01S 15/8918 |
| JP | 2006187631 A | 7/2006 | |
| JP | 2006204923 A * | 8/2006 | ......... G01S 15/8993 |
| JP | 2020531074 A | 11/2020 | |

(Continued)

OTHER PUBLICATIONS

European Extended Search Report in Application 21315271.3, dated Jun. 30, 2022, 11 pages.

(Continued)

*Primary Examiner* — Daniel Pihulic

(74) *Attorney, Agent, or Firm* — Merchant and Gould, PC

(57) ABSTRACT

Examples relate to a method for processing beamformed data of a medium. The beamformed data includes a first set of beamformed data associated with a first spatial region and a second set of beamformed data associated with a second spatial region, and the method includes estimating the clutter caused by the second spatial region at the first set.

16 Claims, 4 Drawing Sheets

(56) References Cited

FOREIGN PATENT DOCUMENTS

WO    2019034436 A1    2/2019

OTHER PUBLICATIONS

Byram, Brett et al., "A model and regularization scheme for ultrasonic beamforming clutter reduction", IEEE Transactions on Ultrasonics, Ferroelectrics, and Frequency Control, IEEE, USA, vol. 62, No. 11, Nov. 1, 2015, pp. 1913-1927.
Viola, Francisco et al., "Time-domain optimized near-field estimator for ultrasound imaging: Initial development and results", IEEE Transactions on Medical Imaging, IEEE, USA, vol. 27, No. 1, Jan. 1, 2008, pp. 99-110.
Holm et al., "Capon Beamforming for Active Ultrasound Imaging Systems", 2009 IEEE 13th Digital Signal Processing Workshop and 5th IEEE Signal Processing Education Workshop, pp. 1-6.
Mola et al., "Time-Domain Optimized Near-Field Estimator for Ultrasound Imaging: Initial Development and Results", NIH Public Access Author Manuscript, IEEE Trans Med Imaging, Apr. 6, 2010, 21 pages.
Feder et al., "Parameter Estimation of Superimposed Signals Using the EM Algorithm", IEEE Transactions on Acoustics, Speech, and Signal Processing, vol. 36, No. 4, Apr. 1988, pp. 477-489.
Japanese Office Action/Summary, Application No. 2022-196389, Jan. 9, 2024, 6 pages.

\* cited by examiner

METHOD AND SYSTEM FOR PROCESSING BEAMFORMED DATA PRELIMINARY CLASS

This application claims the benefit of European Patent Application No. 21315271.3, filed 10 Dec. 2021, and which application is incorporated herein by reference. To the extent appropriate, a claim of priority is made to the above disclosed application.

FIELD OF THE DISCLOSURE

The present invention relates to methods and systems for processing beamformed data, in particular for medical imaging. In particular, the method is suitable for providing image data of a medium scanned by a transducer device. For example, the method may be used in a device such as for instance an ultrasound system.

BACKGROUND OF THE DISCLOSURE

It is known to use a plurality of transducer elements or transceivers (for example arranged as an array) for communication, imaging or scanning purposes, for example in the field of medical imaging, radar, sonar, seismology, wireless communications, radio astronomy, acoustics and biomedicine. One example comprises ultrasound imaging.

The aim of ultrasound imaging is to estimate the medium reflectivity. In a conventional ultrasound imaging method, an ultrasound transducer device (also referred to as an ultrasound probe) with a set of ultrasound transducer elements may be used. In the method, one or multiple transducers are used to transmit one or successively several ultrasound beam into a medium, corresponding to a transmission step. Then, in a reception step a set of backscattered echo signals are received from the medium by the set of transducer elements. In particular, each of the transducer elements converts a received echo signal into for example an electrical signal. The signal may further be processed by the ultrasound system. For example, they may be amplified, filtered digitalized and/or a signal conditioning step may be carried out. The transducer elements may be arranged as a transducer array.

Conventionally, said signals are then transmitted to an image processing system. The received signals may be processed to generate image data of the scanned medium, for example using a beamforming method. Generally, beamforming may be understood as a signal processing technique conventionally used in sensor arrays for directional signal transmission or reception. This process is used to generate beamformed data.

Complex media such as human soft tissues are made of uncountable scatterers. Due to the spatial extension of the incident beam, echoes generated by various scatterers may simultaneously be measured by the ultrasound device. It means that the round-trip propagation times required for an ultrasound wave to travel from the ultrasound device to those scatterers forth and back are the same. The measured signals may then result from the superimposed of various backscattered echoes. As a results, a given area of the beamformed image which corresponds to a spatial region of the medium may be degraded by echoes that have been generated by a different region of the medium. This phenomenon called "clutter" may significantly impair the quality of beamformed data, potentially impacting the displayed images which can in turn result in worse medical diagnostics.

Holm, Synnevåg, and Austeng describe in the article "Capon Beamforming For Active Ultrasound Imaging Systems", 2009 IEEE 13th Digital Signal Processing Workshop and 5th IEEE Signal Processing Education Workshop, Capon beamforming adapted to medical ultrasound imaging. Capon beamforming has improved resolution, i.e. its ability to spatially separate two targets close to each other, compared to traditional beamformers. Capon beamforming impacts the spatial resolution of the beamformer, and a consequence is that it dramatically changes the speckle statistics and the global aspect of the images.

Viola, Ellis, and Walker proposed an adaptive beamformer that aims at reducing the off-axis target impacts in their article "Time-Domain Optimized Near-Field Estimator for Ultrasound Imaging: Initial Developments and Results", IEEE Transactions on Medical Imaging 2008. This beamformer suffers from its computational complexity and it dramatically impacts the speckle statistics as well.

Feder and Weinstein describe in the article "Parameter Estimation of Superimposed Signals Using the EM Algorithm", IEEE Transactions On Acoustics, Speech, And Signal Processing 1988, a computationally efficient algorithm for parameter estimation of superimposed signals based on the Estimate Maximize (EM) algorithm. The algorithm decomposes observed data into their signal components and then estimates the parameters of each signal component separately. The algorithm iterates back and forth, using the current parameter estimates to decompose the observed data better and thus increase the likelihood of the next parameter estimates. The application of the algorithm to the multipath time delay and to the multiple source location estimation problems is considered.

In the algorithm proposed by Feder and Weinstein, delay-and-sum DAS beamformer is presented as a maximum likelihood estimator of the signal backscattered at a location that corresponds to a pixel of the beamformed image. DAS beamforming is only applicable for a single scatterer. A straightforward approach for the maximum likelihood estimation of back scattered signal in that context is not numerically tractable. To cope with that problem, Feder proposed to use E-M algorithm. This scheme is known to have sufficient convergence properties and has demonstrated its efficiency in such problems solving.

The algorithm of Feder and Weinstein is described in the context of passive imaging methods such as e. g. SONAR.

SUMMARY OF THE DISCLOSURE

Currently, it remains desirable to overcome the aforementioned problems and in particular to provide a method and system for processing beamformed data of a medium, in particular for estimating and/or compensating clutter at a (first) selected set of beamformed data. It is thus desirable to provide a method and system which can improve the quality of beamformed data in a computationally efficient manner, for example for facilitating image analysis, helping to set diagnostics, making diagnostics more reliable, and/or improving medical diagnostics.

Therefore, present disclosure relates to a method for processing beamformed data of a medium. The beamformed data comprises a first set of beamformed data associated with a first spatial region and a second set of beamformed data associated with a second spatial region. The method comprises: estimating (f) clutter caused by the second spatial region at the first set.

In one example, a transducer device may be used for acquiring signal data of the medium based on which the beamformed data may be obtained.

By providing such a method it becomes possible to estimate clutter caused by the second spatial region at the first set which is represented by its associated first set of beamformed data. The method may advantageously in particular lead to a more reliable and computationally less complex estimation technique.

It is noted in this context that different beamforming techniques, for example DAS (Delay and Sum) beamforming is sensitive to clutter. The proposed method aims at reducing clutter while maintaining a processing time compatible with real time imaging or data processing.

Moreover, the method may preserve speckle statistics.

Furthermore, the method does not require to iterate back and forth between beamformed data and signal data (for example acquired by a transducer device). Instead, the method may merely process the beamformed data. Accordingly, the method is computationally less complex, as it does not require back-projecting beamformed data to signal data, i.e. to inverse the beamforming process, and then to beamform the signal data again. Avoiding these calculation operations is computationally even more advantageous, in case the method is carried out in a plurality of iterations. Hence, the clutter may be estimated for example in real-time or quasi real-time. Moreover, since the method may be computationally less expensive, the method might also require less processing power and/or energy and/or computing time.

The method may operate on IQ or RF beamformed data (i.e. in-phase and quadrature phase, IQ, and/or radio frequency, RF, beamformed data). As a further consequence, the method advantageously does not require any modifications of the beamformer (for example a DAS beamformer) used to obtain the beamformed data.

Clutter may refer to a measurable quantity, such as an amplitude or an energy of a received wave. For example, clutter may be one or several real values, or (for example in case the method processed beamformed IQ data) one or several complex values.

Clutter may denote for example a parasitic stray signal. Generally, clutter may refer to unwanted echoes in electronic systems, in particular in the transducer device.

The method may further comprise: selecting (d) the first set and determining (e) the second set as a function of the location of the associated second spatial region. In one example, the second spatial region may be located such that the first set is susceptible for clutter generated at the second spatial region.

Additionally or alternatively the method may further comprise: selecting (d') the second set and determining (e') the first set as a function of the location of the associated first spatial region. For example, the first spatial region may be located such that the first set is susceptible for clutter generated at the second spatial region.

In other words, it is possible to determine one or several second sets based on a selected first set, and/or to determine one or several first sets based on a selected second set. Accordingly, both the first set and the second set can be the starting point to determine the other one of the first set and the second. The method may comprise operations (d) and (e), or operations (d') and (e'), or a combination of thereof. In the latter case, for example clutter estimation at some first sets (for example of image pixels) is processed using operations (d) and (e), and for other first sets (for example of image pixels of the same or another image) is processed using operations (d') and (e').

The operations (d) and (e) (and/or respectively (d') and (e')) may be predetermined in advance, i.e prior to processing beamformed data of a particular medium. For example, operations (d) and (e) (and/or respectively (d') and (e')) may be predetermined as a function of characteristics of a transducer device and/or of the shape of the incident beam. The respectively determined calculations may be (pre-) stored (for example in a lookup table or another type of mapping function, as described below). In other words, operations (d) and (e) (and/or respectively (d') and (e')) may merely depend on predefined characteristics of the used transducer device, but not on a specific medium. Merely operation (f) may depend on the medium.

As a consequence, the method may be carried out faster compared to prior art, as the calculations of operations (d) and (e) (and/or respectively (d') and (e')) may be read from a data storage. Hence, the clutter may be estimated for example in real-time or quasi real-time. Moreover, the method may be computationally less expensive and thus might require less processing power and/or energy and/or computing time.

Generally, the beamformed data to be processed in the method may comprise the first and the second set. In other words, the beamformed data may comprise a plurality of sets of beamformed data, wherein each set is associated with a respective spatial region.

A set of beamformed data (for example a first set, second set, etc.) may refer to or may constitute one or more pixels and/or voxels in the beamformed data. The pixels and/or voxels may be represented by 2D image data or higher-dimensional image data or a 2D or higher-dimensional temporal sequence of image data, i.e. video data of arbitrary dimension. A set of beamformed data may also refer or may constitute a group or cluster of pixels or voxels.

It is noted that the numbering "first", "second", etc. of the sets of beamformed data are merely used to distinguish their function in the method of the present disclosure. A given set which has the role of a first set in one embodiment or iteration of the method may have the role of a second set in another embodiment or iteration of the method. For example, assuming that the sets constitute pixels of an image, it may be desirable to estimate the clutter at each pixel. However, the clutter at a given pixel is estimated as a function of other pixels of the same image. Therefore, the same pixel may be a "first set" in a one embodiment or iteration of the method, but may be "a second set" in another embodiment or iteration of the method. Hence, the terms "first set" and "second set" could also be exchanged in the present disclosure.

The first and/or second spatial region(s) may be regions of the medium or may be associated with regions of the medium. However, the first and/or second spatial region(s) may also be defined as a function of a used transducer device. In the latter case, the regions may be defined independently from a specific medium but merely as a function of the geometry of the transducer device, in particular of its transducer array.

In other words, a spatial region may correspond to a physical region of scatterer(s) or reflector(s) in the medium, meanwhile a set of beamformed data may correspond to a position in image data.

The present disclosure may cover the scenario, in which a scatterer located at a single second region directly causes clutter at the first set. This phenomenon may arise if the first and second spatial region are characterized by the same round trip propagation time. This time is defined as the sum of the transmitted propagation time, i.e. the delay required for a given incident beam to travel from the ultrasound device to a spatial region of interest; and the received propagation time, i.e. the delay required for echoes generated at this spatial region of interest to travel back to a given transducer element of the ultrasound device.

However, also multiple scattering scenarios may be covered by the present disclosure. In such scenarios, multiple scatterers located at multiple second spatial regions may generate echoes that have been scattered multiple times and may cause clutter at the first set. In other words, these echoes follow multiple scattered path that have the same propagation time the echoes associated to the first spatial region.

Exemplary mediums comprise inert materials but also body part(s) such as a liver, a breast, muscles (muscle fibres) of a human or an animal. In particular, any strong reflectors such as medium interfaces (e.g. walls of organs) can imply an increased reflectivity which might in return lead to clutter at other regions.

The method may be applicable to any shape of emission waves. In particular, it can be apply to focused wave, diverging wave or plane wave. Note that clutter generated by plane wave and diverging wave is usually more significant.

Beamforming may be referred to as a signal processing technique used to process signal data of a transducer device. Beamforming may in particular be used to process RF signal data of a transducer device to create a spatial model of a medium, e. g. for obtaining image data of the medium, e. g. a human tissue.

Beamformed data may accordingly be data in the spatial domain, in particular in a two or three dimensional (2D/3D) spatial domain, to represent the medium. The signal data acquired by a transducer device may be in the time domain and/or in a space-time domain. For example, the signal data may be described according to two dimensions wherein one dimension reflects the acquisition time and the other one the spatial location of the transducer element of the ultrasound device that acquired the signal.

The method may further comprise the following step:
compensating (g) the estimated clutter at the first set, and/or
removing (g') the clutter at the first set.

By including the above method operations (g) and/or (g'), it becomes possible to compensate the estimated clutter at the first set and/or to remove clutter at the first set. This may allow to improve the quality of the beamformed data by removing the impact of clutter. This can for example facilitate diagnostics, make diagnostics more reliable, and/or improve medical diagnostics.

The clutter may be estimated as a function of the location of the first spatial region and/or of the location of the second spatial region. For example, if the location of both the first and the second spatial region is taken into account, also a relative distance between these regions may be determined.

In one example, the locations of the first and/or second spatial region may be defined in relation to the position of the used transducer device.

The clutter may be estimated as a function of the second set and/or the amplitude of the second set. For example, an increased amplitude (i.e. an increased intensity or energy level) may lead to the estimation of an increased clutter.

Generally, the second spatial region may be associated with the second set. Accordingly, the second spatial region may be represented by the second set. Therefore, the clutter at the first set may be determined as a function of the second set.

In particular, the second set may be considered for estimating the clutter, (desirably only) in case the amplitude of the second set exceeds a predefined threshold. Accordingly, operation (e) may comprise a pre-selection and/or filtering of second sets with an increased amplitude. This may simplify the method and reduce computational costs at similar or only slightly worse results as it is possible that only second regions (as for example described below) having a reflectivity exceeding a predetermined threshold contribute significantly to the clutter at the beamformed data representing the first region. Other regions may be disregarded in the estimation operation (f). It is furthermore possible to consider first (and/or to prioritize) second sets exceeding the threshold. Optionally, other second sets may be considered afterwards (and/or with less priority), for example to render the estimated clutter more accurate.

The second set of beamformed data may be associated to signal data received from the medium which is isochronous to signal data received from the medium associated with the first set. The signal data may be in the time domain. The signal data may be hence RF signal data.

In other words, the second set of beamformed data may be associated to signal data received from the medium which share a certain temporal relation to signal data received from the medium associated with the first set, e.g. are isochronous.

Accordingly, the term isochronous may describe that for a first spatial region, signals from the second set may be isochronous and may hence share the same propagation time. Said propagation time may be i. e. a time period between transmitting a signal by the transducer device and receiving a response signal. In particular, said propagation time may refer to a time period between a pulse emission by one or a plurality of transducer elements and a reception of an echo signal from scatterer in the medium by a transducer element. For example, each receiving transducer element may be individually considered. The signals associated with the first and second set may have the same propagation time, i.e. are isochronous, at the receiving transducer element. Hence, the signals associated with the second set can cause clutter at the first set, or in other words, the first set may be susceptible for clutter generated at the second region.

Performing ultrasound measurements may comprise transmitting an emitted sequence ES of ultrasound waves into the medium, receiving a response sequence RS of ultrasound waves from the medium, wherein the ultrasound signal data may be based on the response sequence RC of ultrasound waves.

In case the second set of beamformed data may be associated to signal data received from the medium which is isochronous to signal data received from the medium associated with the first set, this may allow to estimate clutter that is related to the emitted sequence of ultrasound waves.

Determining (e) the second set of beamformed data may comprise: determining (e) a plurality of second sets of beamformed data respectively associated with a plurality of second spatial regions that are located such that the first set is susceptible for clutter generated at the second spatial regions.

For example, based on a selected first set (for example an image pixel), a plurality of second sets (for example further adjacent pixels) may be determined.

Estimating (f) the clutter at the first set may comprise: estimating (f) a plurality of clutter contributions respectively associated to the second sets, the clutter at the first set being a function of the plurality of clutter contributions.

In particular, the plurality of second spatial regions may be different to each other, i.e. may be at different locations of the medium. Hence, clutter contributions caused by different (second) regions of the medium may be considered to estimate a total or summed clutter.

Furthermore, this allows a clutter estimation that includes clutter contributions of a plurality of second spatial regions, e. g. a proportion of or all second spatial regions that are located such that they can cause clutter at the first set.

The (total or summed) clutter at the first set may be estimated by a linear combination of the plurality of clutter contributions. For example, clutter contribution from a second spatial region being farer away from the first region may be weighted less than clutter contribution from a second spatial region being closer to from the first region. The closer second region may namely have a stronger influence. Accordingly, the resulting estimation of the total clutter can become more accurate.

For example, the linear combination/c may be expressed by the following equation (1):

$$lc = \Sigma_i a(i) * b(i) \quad (1),$$

wherein i refers to a selected second spatial region, $a(i)$ denotes the computed clutter contribution associated to the spatial region i and $b(i)$ denotes a respective weighted coefficient.

According to a further example, the weighted coefficients may be determined based on a mathematical model that may be based on relevant laws of physics and/or parameters that describe aspects of the data taking, such as aspects related to the transducer device and/or the medium and/or the emitted signal and/or the received signal.

In a corresponding manner, and in particular with reference to operations (d') and (e'), determining (e') the first set of beamformed data may comprise: determining (e) a plurality of first sets of beamformed data respectively associated with a plurality of first spatial regions that are located such that each first set is susceptible for a clutter contribution generated at the second spatial regions.

Estimating (f') the clutter contribution at each first sets may comprise: estimating (f') a plurality of clutter contributions respectively associated to the first sets. Accordingly, based in the selected second set, the clutter contribution caused by the second spatial region associated with said second set may be determined at the concerned first set. A total clutter at any one of the first sets may then be calculated by summing clutter contributions caused by different second spatial regions.

The method may further comprise before selecting (d, d') the first and/or the second set: processing (c) ultrasound signal data of the medium to obtain the beamformed data. Instead of ultrasound signal data also any other type of signal data originating from a transducer device may be used.

The method may further comprise, before processing (c) ultrasound signal data or selecting (d) beamformed data, transmitting (a) an emitted sequence (ES) of ultrasound waves (We) into the medium (11), and receiving (b) a response sequence (RS) of ultrasound waves (Wr) from the medium. The ultrasound signal data may be based on the response sequence (RS) of ultrasound waves (Wr).

Determining (e) the first and/or second set and/or estimating the clutter (f) may be further based on at least one of:
the geometry of a transducer device (in particular of its transducer array) used for acquiring data of the medium on which the beamformed data are based,
the arrangement and/or size (for example the width) of the single transducer elements of the transducer device,
any further predefined characteristics of the transducer elements, for example predefined characteristics of their respective piezo elements,
the emission and/or receive aperture of the transducer device,
the emission duration,
the wavelength and/or type of emission pulse (or respective emitted wave or respective acoustic beam) on which the beamformed data is based,
predefined characteristics (for example the geometry) of the emitted wave front (for example the angle of an emitted planar wave with regard to the emitting transducer device), and
a predetermined speed of sound model of the medium that has been used for the beamforming process.

The above-mentioned characteristics may also be referred to as predefined parameters of the acquisition sequence. This may allow to obtain a more accurate and/or more precise estimation of clutter. In particular, by taking into account at least one of these predefined parameters of the acquisition sequence, for any selected first set, all second sets may be (pre-)determined and for example stored in a lookup table or the like.

Each set of beamformed data may be associated with at least one pixel or voxel.

The beamformed data may be beamformed IQ data (i.e. in-phase and quadrature phase, IQ, data) and/or beamformed RF data (i.e. radio frequency, RF, data).

Accordingly, a set of beamformed data may for example comprise or consist of at least one set of an in-phase and a quadrature phase value.

In case the beamformed data are arranged in the form of a two- or three-dimensional matrix, each pixel (in two dimensions) or each voxel (respectively in three dimensions) may comprise or may be defined by a respective set of beamformed data.

The first and/or second set and/or the first and/or second spatial region may be predetermined. For example, the first and/or the second spatial region may be predetermined as a function of any of the above-mentioned parameters of the acquisition sequence (for example its geometry).

The relation between the first and the second spatial region (i.e. position(s) of second spatial region(s) for a selected first spatial region) may be stored in a respective mapping function, e.g. in a lookup table. In other words, operations (d) and (e) (and/or respectively operations (d') and (e')) may be predetermined/pre-calculated and stored, e.g. in look up tables/mapping functions, independently of the specific beamformed data of the medium. When the method is applied to a specific medium, the selection of the second spatial region for a given first set and/or the selection of the first spatial region for a given second set may be determined by using said mapping function.

The method may be performed for a plurality of first sets, in parallel and/or in series.

This may allow to estimate clutter at a plurality of first sets, e. g. for a part of or for the entirety of the beamformed data. The part may be for example a region of interest in the beamformed data. After estimation, the clutter may be compensated at the first sets. These ameliorated beamformed data may then be graphically represented and/or further processed.

The method may be performed for the first spatial region (or the plurality of first sets, as described above) in several iterations. At each iteration, modified beamformed data may be obtained by compensating the estimated clutter, in particular at the plurality of first sets. The modified beamformed data obtained in a first iteration is used in a subsequent second iteration. In a first default example, the method may comprise one or more iterations. In a further example, the method may comprise a plurality of iterations with a range of two to seven. With two iterations, the estimation may already be enhanced, and more than seven iterations do not necessarily lead to a significant amelioration in view of the additional computational costs. In a more specific example, the method may comprise three iterations, what appears to be an advantageous tradeoff between optimisation of the clutter estimation and limitation of the required computational costs.

Accordingly, with each iteration, the clutter may be increasingly compensated.

The number of applied iterations may be fixed and/or any predefined converging rule and/or threshold may be used to determine the number of iterations or to define a stop criteria.

An AI (Artificial Intelligence) based model, for instance a machine-learning model like for example a neural network, may be trained based on an estimated clutter. The machine-learning model may be further trained based on any essential and/or optional feature of the method described above, as e. g. location of first and/or second spatial region, reflectivity of the second spatial region, geometry of a transducer device used for acquiring data of the medium on which the beamformed data are based, the arrangement of the signal transducer elements of the transducer device, the emission and/or receive aperture of the transducer device, the wavelength and/or type of emission pulse on which the beamformed data is based, the geometry of the emitted wave front, look-up tables that store regions from which clutter is generated, etc.

The AI based model may be used for estimating clutter and/or compensating and/or removing an estimated clutter.

Using an AI based model for estimating clutter and/or compensating and/or removing an estimated clutter may provide results of a similar quality at reduced computational costs.

A trained AI-based model may be evaluated by using beamformed data associated with planar waves for scanning a medium as input data, and by comparing the output data of the AI model with beamformed data associated with focalized waves for scanning the same medium as output data. Since the beamformed data associated with focalized waves are less impacted by clutter, they may provide a good reference for the output data of the AI-based model.

Generally, two types of acquisitions of a medium may be used to obtain two types of beamformed data respectively, i.e. beamformed data associated with (1.) acquisitions using plane waves, and (2.) acquisitions using focalized waves of the same medium.

According to an example, the method of the present disclosure may be applied to beamformed data of both (1.) and (2.). The results of estimated clutter and in particular of the compensation of clutter may then be compared, for example for evaluating the efficiency of the method. In this case, the compensation of clutter should be much more significant at (1.) and should converge towards the beamformed data of (2.).

It is also possible to obtain several times beamformed data of (1.) and once of (2.) of the same medium. The beamformed data of (2.) may be used to calibrate and/or validate the compensation method which compensates the several beamformed data of (1.).

The present disclosure further relates to a computer program comprising computer-readable instructions which when executed by a data processing system cause the data processing system to carry out the method may be used.

The present disclosure further relates to a system for processing beamformed data of a medium. The beamformed data comprise a first set of beamformed data associated with a first spatial region and a second set of beamformed data associated with a second spatial region. The system comprises a processing unit configured to:
  estimate (f) the clutter caused by the second spatial region at the first set.

The system may comprise the transducer device. The system may comprise in particular a probe (for example an ultrasound probe) which may comprise the transducer device(s).

The system may be an ultrasound system.

The system may comprise further functional characteristics and/or may be configured in correspondence to the method operations described above.

The disclosure and its embodiments may be used in the context of medical systems dedicated to human beings, plants or animals but also any (non-living) soft material to be considered.

It is intended that combinations of the above-described elements and those within the specification may be made, except where otherwise contradictory.

It is to be understood that both the foregoing general description and the following detailed description are exemplary and explanatory only, are provided for illustration purposes and are not restrictive of the disclosure, as claimed.

The accompanying drawings, which are incorporated in and constitute a part of this specification, are provided for illustration purposes, and illustrate embodiments of the disclosure and together with the description and serve to support and illustrate the principles thereof.

DESCRIPTION OF THE EMBODIMENTS

Reference will now be made to exemplary embodiments of the disclosure, examples of which are illustrated in the accompanying drawings. Wherever possible, the same reference numbers will be used throughout the drawings to refer to the same or like parts. Moreover, the features explained in context of a specific embodiment, for example that one of FIG. 1, also apply to any one of the other embodiments, when appropriate, unless differently described.

Figure 1:
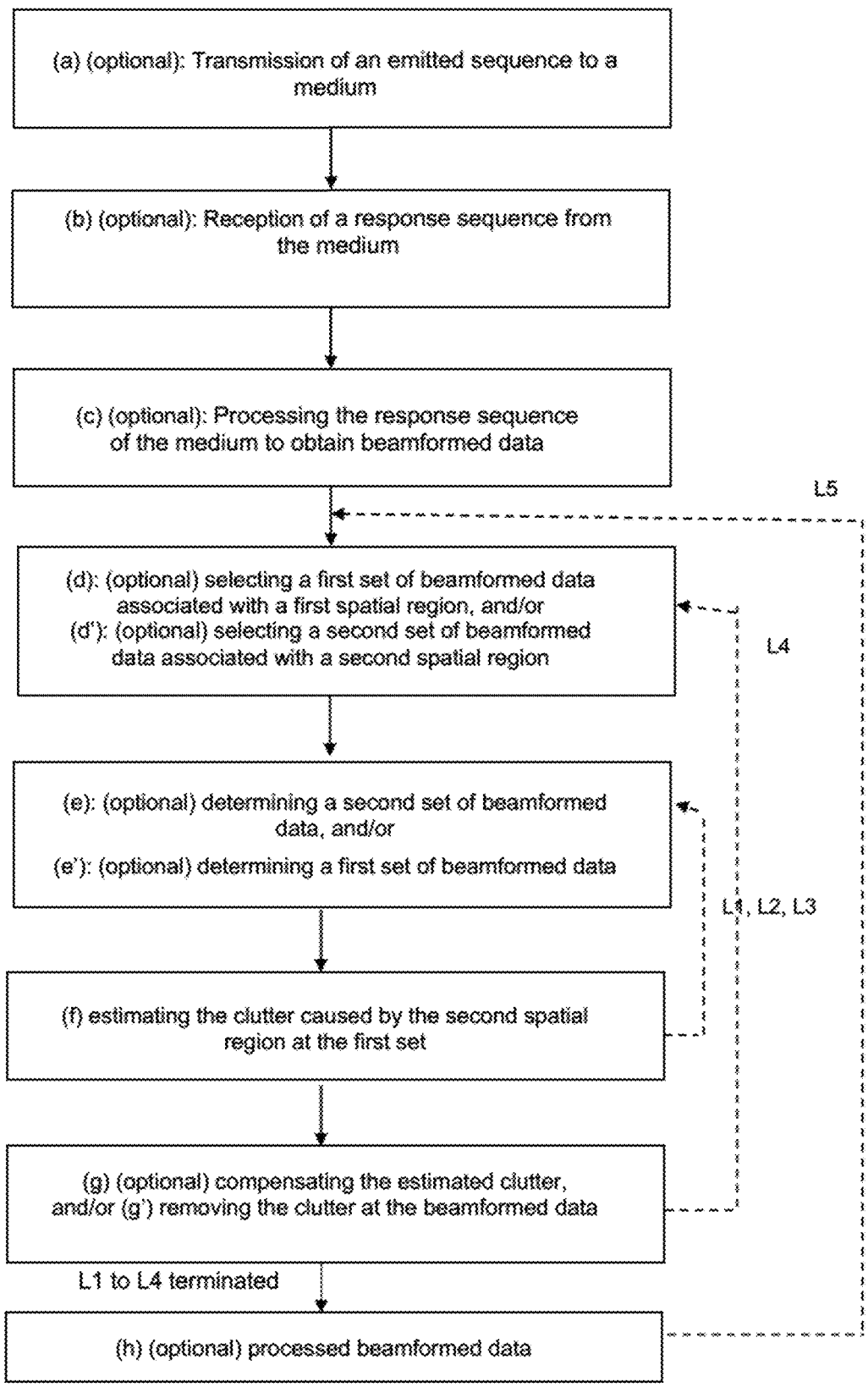
FIG. 1 shows an exemplary embodiment of a method according to embodiments of the present disclosure.

FIG. 1 shows an exemplary embodiment of a method according to embodiments of the present disclosure. The method may be carried out by means of a system 1, more in particular by an ultrasound system 20. An example of an ultrasound system is described in context of FIG. 2.

The method may be an ultrasound method carried out by an ultrasound system. Possible ultrasound methods comprise B-mode imaging, shear wave elastography imaging (such as ShearWave® mode developed by the applicant, Doppler imaging, M mode imaging, CEUS imagine, Ultrafast™ Doppler imaging or angio mode named under Angio P.L.U.S™ ultrasound imaging or any other ultrasound imaging mode. Accordingly, different acquisition modes may be used to obtain signal data based in which the beamformed data may be determined. The method may be part of any of the above-mentioned methods or may be combined with any of these methods.

However, the method according to the present disclosure may also be applied to other technical fields than ultrasound examination. In particular, any technical field is possible which uses a plurality of transducer elements to acquire data/signals of an examined medium or environment and/or which may use a beamforming technique based on the collected data/signals. Examples comprise methods using a radar system, sonar system, seismology system, wireless communications system, radio astronomy system, acoustics system, Non-Destructive Testing (NDT) system and biomedicine system or any other technique in the field of active imaging. The principle of active imaging, i.e. of emitting pulses into a medium via one or several elements (sources) and receiving response pulses via one or several elements (receiver) and to estimate and/or compensate a clutter is similar to the functionalities of an ultrasound transducer.

Accordingly, the method according to the present disclosure may in each of these cases achieve the same positive technical effects as described above, for example of compensating undesired clutter at beamformed data. However, for mere illustration purposes of the present disclosure, in the following it is referred to the example of an ultrasound method.

The method may be for example a method for compensating clutter in beamformed data of a medium, and more in general for processing beamformed data.

In an optional operation (a) at least one pulse is transmitted into a medium. For example, the transmission step may comprise insonification of the medium with a cylindrical wave that focuses on a given point and/or plane waves of different angles. More in particular, in the transmission step a plurality of ultrasonic waves may be transmitted into an imaged region.

Generally, in the present disclosure a pulse may correspond to an acoustic or electrical signal emitted by a transducer element. The pulse may for example be defined by at least one of: the pulse duration, the frequency of the resulting wave, the number of cycles at the given frequency, the polarity of the pulse, etc. A wave may correspond to the wavefront generated by one or several transducer elements (i.e. by respectively emitted pulses). The wave may be controlled by means of emission delay between the different used transducer elements. Examples comprise a plane wave, a focused wave and a divergent wave. A beam may correspond to the physical area insonified by the wave (for example in the medium). Hence, the beam may be related to the wave but may have less or no temporal notion. For example, it may be referred to a beam when the depth of field of a focused beam is of interest.

In an optional operation (b), a response sequence is received from the medium by the set of transducer element(s). The response sequence may comprise backscattered echoes of the insonification of operation (a). The response sequence may also be referred to as signal data, in particular ultrasound signal data and/or RF and/or IQ signal data. The signal data may be in the time domain, more in particular in a spatio-temporal domain, as for example described in more detail below. In one example, the response sequence may be processed by bandpass filtering, in order to keep only one or several frequency ranges.

In an optional operation (c), the response sequence is processed to obtain beamformed data. Beamformed data may be data in the spatial domain, in particular in a two- or three-dimensional spatial domain, to represent characteristics of the medium. For example, in the case of B-mode imaging, the beamformed data is an estimation of the medium reflectivity. In one example, in case a plurality of beamformed data collections are obtained for a respective plurality of frequency ranges (as explained above), the beamformed data may be defined as a function of frequency.

It is noted that operations (a) to (c) are optional, as they may also be carried out by any other system than the system used for operations (d) to (f) or at another time. Data may also be provided by other functionalities such as simulation devices, insonification on a phantom, etc. It is also possible that the beamformed data are pre-stored, and for example provided by/read on a data storage, a communication interface, etc.

In optional operation (d) a first set of beamformed data associated with a first spatial region of the medium is selected. It is also possible to select a second set of beamformed data associated with a second spatial region of the medium in an optional operation (d'). Said selection may be controlled by a predefined selection algorithm, as for example described in more detail below.

In optional operation (e) (in particular following operation (d)) a second set of beamformed data associated with a second spatial region of the medium is determined. Said second region is located such that it may cause clutter at the first set, or in other words, such that the first set is susceptible for clutter generated at the second spatial region. Accordingly, based on the location of the first and second spatial region, it may be determined, in operation (e), whether the (second) region would generally be able to cause clutter at the first set or not. In case operation (d) is replaced by operation (d'), it is further possible in an optional operation (e') to determine a first set of beamformed data associated with a first spatial region of the medium. The further features of the method may be adapted, respectively.

Optionally, operations (d) and (e) or both of them may be carried out in advance. In other words, these operations may be carried out once for a given transducer device, a given acquisition sequence and a given beamforming process and may then be valid for any medium. This is possible, since these operations does not depend on characteristics of a specific medium. Therefore, the calculations of these operations may be stored for the specific transducer device, acquisition sequence and beamforming process. Once the method is applied to specific medium, the calculations of these operations (d) and (e) may be read from a data storage. It is also possible to store respective calculations for different types of transducer devices.

In one example, for each first region the respectively (pre-)determined second regions may be stored in a look-up table or other form of mapping. The look-up table may be usable right after determination or in the future, locally or remotely.

In operation (f) the clutter caused by the second spatial region at the first set is estimated. Accordingly, in this operation, it is estimated, whether the second spatial regions actually cause clutter or not, and optionally also to which extent (i.e. amplitude or/and amount of clutter).

As stated above, for a given first spatial region and speed of sound model used for the beamforming process, there may be multiple second spatial regions that are susceptible to cause clutter at the first set for a given emission and a given received transducer. In some beamforming process, signals generated by multiple emitted waves and measured by multiple transducers are used to generate the first set of beamformed data. In this case, clutter contribution arises from multiple second spatial regions may be estimated for each emitted waves and received transducer used to beamform the first set.

According to a first option, the operations (e) and (f) may be repeated via loop L1 over the spatial second regions for a given emitted waves and received transducer and may hence be carried out for several iterations. In each iteration a different second spatial region may be determined in operation (e) and a respective clutter contribution of said second region may be estimated in operation (f). Accordingly, in one example, a total or summed clutter at the first set may be estimated by a linear combination of the plurality of clutter contributions.

Figure 2:
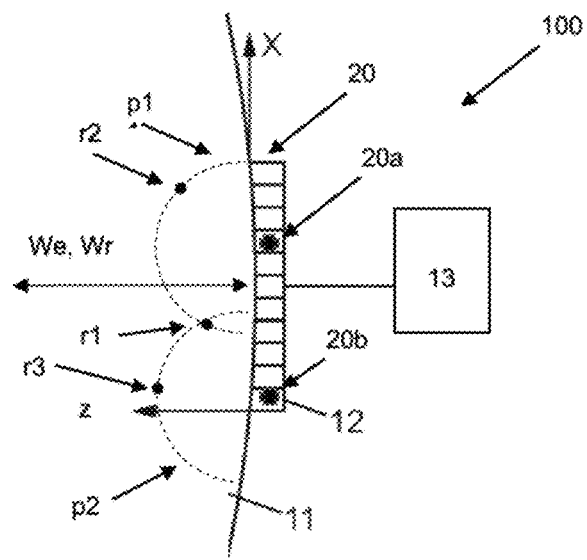
FIG. 2 shows a system carrying out a method according to an exemplary embodiment of the present disclosure.

According to a second option, the operations (e) and (f) may be repeated via a further loop L2 over the receiving transducer elements and may hence be carried out for several iterations. In each iteration, an ensemble of second spatial regions may be determined for a given (different, receiving) transducer element of the transducer device used for determining the first set of beamformed data. A respective clutter may be estimated for said transducer element in operations (e) and (f). As shown in FIG. 2, the method may namely be applied to a single transducer element. The method may hence be repeated to consider a plurality of transducer elements. Said plurality of transducer elements may comprise all transducer elements of the transducer device or only those transducer elements whose signal data are used for determining the first set of beamformed data. The loop L2 may comprise the loop L1. In other words, in each iteration of loop L2, the iterations according to loop L1 may be included.

According to a third option, the operations (e) and (f) may be repeated via loop L3 over emitted waves and may hence be carried out for several iterations, for example in case of synthetic beamforming. In each iteration, another emitted wave may be considered. Hence, the operations (e) and (f) may be iterated over the number of transmitted waves used to beamform the first set. A wave may be generated by one or several transducer elements. For example, the transducer device may generate planar emission waves with different predefined emission angles. A beam may also be referred to as the area through which the sound energy emitted from the transducer device travels. The loop L3 may comprise at least one of or all of the loops L1 and L2. In other words, in each iteration of loop L3, the iterations according to loops L1 and L2 may be included.

Note that loop L1, L2, L3 may be processed in various order and combined in order to estimate a total clutter at the first set that arises from the combination of clutter contributions generated by each one of the second spatial regions determined by the loop L1, L2 and L3.

It is also possible that at least one of loops L1 to L3 comprises an iteration from operation (e) to operation (g) (or alternatively (g')), instead of from operation (e) to operation (f). Accordingly, in each iteration, the estimated clutter may be compensated and/or removed in operation (g),(g').

In an optional operation (g) the estimated clutter is compensated at the beamformed data. In particular, in an optional operation (g') the clutter may be removed at the beamformed data. It is however also possible that the clutter is compensated only in part.

According to a fourth option, the operations (d) to (g) (or alternatively (g')) may be repeated via loop L4 and may hence be carried out for several iterations. In each iteration a different first set associated with a respectively different first spatial region may be selected in operation (d). A respective clutter caused by a determined second spatial region may be estimated in operation (f) and compensated and/or removed in operation (g), (g'). For example, a predefined selection algorithm may select different first regions on a coordinate system of the beamformed data, for example in a stepwise manner. In this way, clutter may be estimated across a spatial region of interest in the beamformed data or across the complete spatial extension of the beamformed data. The loop L4 may comprise at least one of or all of the loops L1 to L3. In other words, in each iteration of loop L4, the iterations according to loops L1 to L3 may be included.

It is also possible that loop L4 comprises an iteration from operation (e) to operation (f), instead of from operation (e) to operation (g),(g'). Accordingly, in each iteration of loop L4, the estimated clutter may be merely estimated in operation (f). Once the clutter has been estimated for the plurality of first sets (for example for the entirety of beamformed data), the clutter may be compensated and/or removed respectively for the plurality of first sets in operation (g),(g').

It is further possible that the iterations of at least one of loops L1 to L4 are parallelly processed.

In case operations (d) and (e) are replaced by operations (d') and (e'), the iterations of loops L1 to L4 may be adapted by respectively exchanging the first set by the second set and the second set by the first set.

In an optional operation (h) processed beamformed data may be obtained. This may in particular be the case, once the iterations of (at least one of or all of) loops L1 to L4 are terminated. As a result, the entirety of beamformed data may be processed. For example, the processed beamformed data may be displayed (for instance to a user of the system described in context of FIG. 2) and/or may be further processed. For example, the processed beamformed data may be provided to another system or module, for instance an algorithm or AI-based model.

According to a fifth option, the operations (d) to (h) may be repeated via loop L5 and may hence be carried out for several iterations. In each iteration processing of the beamformed data according to operations (d) and (h) may be repeated. Accordingly, the loop L5 may comprise at least one of or all of the loops L1 to L4. In other words, in each iteration of loop L5, the iterations according to loops L1 to L4 may be included. At each iteration, modified beamformed data may be obtained by processing the beamformed data obtained in a previous iteration. In other words, the modified beamformed data obtained in a first iteration may be used in a subsequent second iteration. Accordingly, with each iteration, the clutter may be more accurately estimated and compensated.

The method may also be carried out using any combination of loops L1 to L5.

FIG. 2 shows a system carrying out a method according to an exemplary embodiment of the present disclosure.

The system 100 may for example be configured to obtain and process beamformed data of a medium 11, or for instance for the purpose of imaging an area in a medium 11.

The medium 11 is for instance a living body and in particular human or animal bodies, or can be any other biological or physic-chemical medium (e.g. in vitro medium). The medium may comprise variations in its physical properties. For example, the medium may comprise a liver, breast, muscles (muscle fibers), and in particular any interfaces in the medium (e.g. walls of organs). Such interfaces can namely have an increased reflectivity which might in return lead to clutter at other regions.

The system 100 may include a probe 12 comprising at least a transducer device, for example an ultrasound transducer device. Said transducer device may comprise one or a plurality of transducer elements 20, for example in the form of a transducer array arranged along an x-axis. Each transducer element 20 may be adapted to transform a signal into an ultrasound wave (emit) and/or to transform an ultrasound wave into a signal (receive).

The system 100 may further include an electronic processing unit 13. Said unit may optionally control the transducers in the probe in any mode (receive and/or emit) in the case the same probe is used for emission/reception. Different probes may also be used, either for emission/reception or for appropriate adaptation to scanned medium. Emit and receive transducer elements may be the same, or different ones, located on one single probe or on different probes.

Furthermore, the unit 13 may process ultrasound signal data, and determine characteristics of the medium and/or images of said characteristics.

The probe 12 may comprise a curved transducer so as to perform an ultrasound focusing to a predetermined position in front of the probe into a direction of a z axis. The probe 12 may also comprise a linear array of transducer. Moreover, the probe 12 may comprise few tens of transducer elements up to several thousand (for instance 128, 256, or 8 to 2064) juxtaposed along an x axis so as to perform ultrasound focusing into a bi-dimensional (2D) plane. The probe 12 may comprise a bi-dimensional array so as to perform ultrasound focusing into a tri-dimensional (3D) volume. Moreover, the probe may also comprise several transducer devices, for example at least one for emission and at least one for reception. In another example, the probe 12 may comprise a single transducer element. In another example, the probe 12 may comprise a transducer device in a matrix form (comprising in this case for example up to several thousand transducer elements).

The above processing unit 13 and the probe 12 may be configured to send an emitted sequence ES of ultrasound waves We into the medium 11, using for example one transducer elements 20 or a predefined group of transducer element 20. The above processing unit 13 and the probe 12 may further be configured to receive a received sequence RS of ultrasound waves (i.e. ultrasound signal data) from the medium, using for example one transducer element 20 or a predefined group of transducer elements 20 (the same or another than that one used for emission).

The ultrasound waves We, Wr toward and from the location may be a focused wave (beam) or a non-focused beam. In this context, a pre-defined beamforming method may be used, for example: The emitted ultrasound wave We may be generated by a plurality of transducers signals that are delayed and transmitted to each transducer of a transducer array. The received ultrasound wave Wr may be composed of a plurality of transducer signals that are combined by delay and summation to produce a received sequence RS.

In a possible embodiment of the method of FIG. 1 specific transducer element 20*a* may be considered. A clutter caused by a second spatial region r2 at a first set of beamformed data associated with a first spatial region r1 may be estimated.

As shown in FIG. 2, for a given emission wave (or the respective acoustic beam) the echo signal from both regions r1 and r2 may have the same round trip propagation time for the received transducer element 20*a*. Accordingly, the signal data received from the first region r1 may be isochronous to signal data received from second region r2. Hence, since the signals associated with the respective first and second set have the same propagation time for the transducer element 20*a*, the signals associated with the second set can potentially cause clutter at the first set. In a simplified manner, it may be said that region r2 is isochronous to region r1 for a given transducer element and a given emission wave.

Due to this isochronous characteristic, the second set of beamformed data associated with the second spatial region r2 is located such that the first set is susceptible for clutter generated at the second spatial region r2. In other words, an area (or location) may be determined on which any second regions are located which can generate clutter at the first set. In one example, said area may have the form of a parabola p1 (for example in case of a planar emission wave). However, the area may also have any other form, for example of an ellipse. Generally, the area may be determined as a function of at least one of the selected first set, the considered transducer element, the geometry of the transducer device (or more in particular its transducer array), the emission wave (or the respective acoustic beam), and a predetermined propagation speed model of the medium.

In one example, the propagation speed c may be assumed to be constant in the medium. In another example, the propagation speed c may be determined by a propagation speed model. If for example the medium is known, speed values may be attributed to different areas of the medium, for instance to muscles, etc.

It may be assumed in the present disclosure that the size of the transducer element may be relatively small in comparison to the wavelength of the emitted waves and/or their spatial pulse length. The spatial pulse length of an emitted wave may also determine the width of the above-mentioned area, i.e. of the exemplary parabola p1 on which second regions are located.

In order to estimate the clutter (in particular to evaluate whether there exist really clutter caused by r2), the second set of beamformed data associated with r2 may be taken into account, in particular the amplitude (or energy level) of said second set. In other words, the clutter may be estimated as a function of the second set and/or the amplitude of the second set. It is further possible to take the position of the r1 and r2 into account. For example, the closer they are located to each other and/or the closer the second region r2 is to a point directly ahead of the considered transducer element (in the direction z), the more the clutter contribution of said second region r2 may be weighted. Furthermore, in case the amplitude of the second set does not exceed a predefined threshold, r2 may be completely disregarded in the estimation operation. Generally, characteristics of r1 and r2 (for example their respective amplitude or location) may be determined in the associated beamformed data, i.e. in the first and second set of beamformed data.

A corresponding exemplary scenario is shown for transducer element 20*b* in view of spatial regions r1 and r3 being located on a parabola p2 relevant for the transducer element 20*b*. Accordingly, for transducer element 20*b* the clutter caused by the third spatial region r3 may be estimated at the first set. In other words, in order to estimate the clutter at the first set, a plurality of transducer elements 20*a*, 20*b* may be considered. Said plurality of transducer elements may comprise all transducer elements of the transducer device or only those transducer elements whose signal data are used for determining the first set of beamformed data (cf. also the iteration over loop L2, as explained above).

Figure 3:
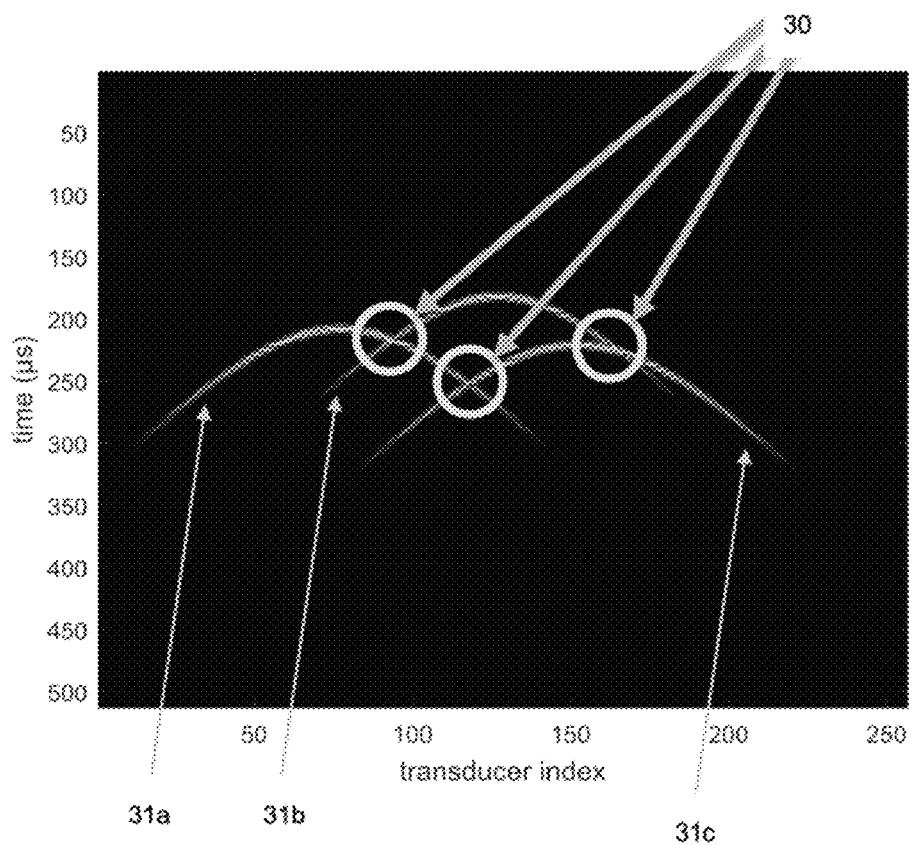
FIG. 3 shows an example of RF signal data of a medium with three reflectors.

FIG. 3 shows an example of RF signal data of a medium composed by three reflectors. The RF signals have been measured in this example by a linear array and results from the insonification of this medium with a plane wave of incident angle equal to 0 with regards to the ultrasound array. In this example the RF signal data are in the form of a two-dimensional matrix. The signal data may be in the time domain or more in particular in a space-time domain. The signal data may have hence two dimensions wherein one dimension (in FIG. 3 the vertical axis) reflects the acquisition time and the other dimension (in FIG. 3 the horizontal axis) reflects the spatial axis of the transducer array of the used transducer device (i.e. in FIG. 2 the X-axis). Said signal data of FIG. 3 may be acquired by a transducer device, as for example shown in FIG. 2.

The example of FIG. 3 shows signal data received from a medium with three point reflectors leading to three arched signal responses 31a, 31b, 31c.

Figure 4:
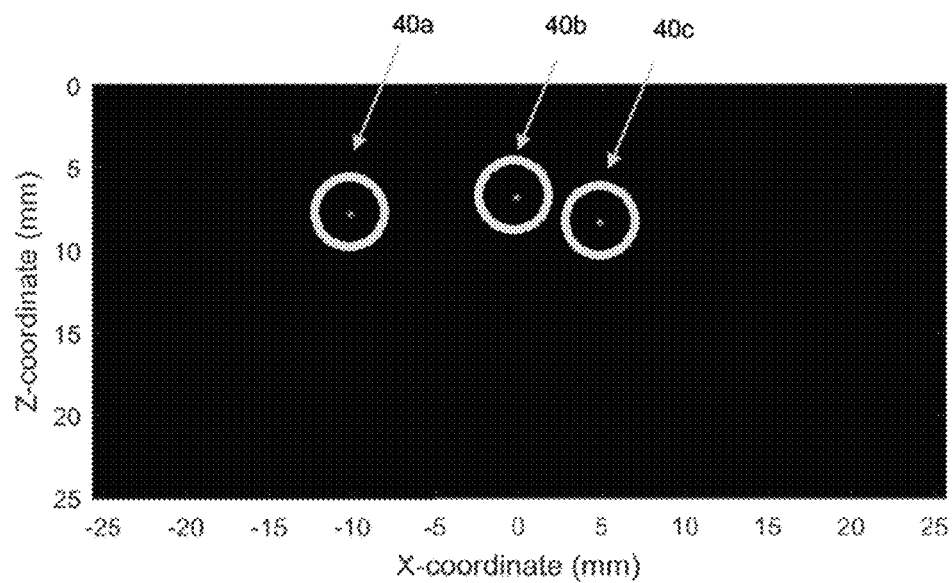
FIG. 4 shows the beamformed data of the RF signal data of the FIG. 3.

FIG. 4 shows the beamformed data of the RF signal data of the FIG. 3. Said beamformed data are in the spatial domain. The beamformed data may have two dimensions wherein one dimension (in FIG. 4 the vertical axis) reflects the depth direction of the medium (i.e. in FIG. 2 the Z-axis) and the other dimension (in FIG. 4 the horizontal axis) corresponds to the axis of the transducer array of the used transducer device (i.e. in FIG. 2 the X-axis).

The beamformed data may be obtained by a Delay And Sum (DAS) beamformer, as shown in equation (2):

$$o(x, z) = \frac{\sum_{n=0}^{N-1} \alpha_n s_n(t - \tau_n)}{\sum_{n=0}^{N-1} \alpha_n^2} \quad (2)$$

where:
$\tau_n$ is the estimated round-trip propagation time for the incident wave to travel to point (x,z) and to back-propagates toward the transducer element n, and
$\alpha_n$ is the apodization coefficient linked to (x, z) and transducer element n An example of an optimum result of the beamformed data is shown in FIG. 4 which illustrates the three beamformed pixels 40a, 40b, 40c (each one highlighted by a circle), which represent the reflectors in the medium.

However, the DAS beamformer is optimal in case of a single point reflector only. Therefore, in the example of FIG. 3, the multiple (i.e. in FIG. 3 three) point reflectors result in clutter blurring images and degrading contrast. This may be in particular due to the overlapping sections 30 of the arch signals 31a, 31b, 31c. As a consequence, the beamformed data of FIG. 4 would in reality be deteriorated by clutter.

Figure 5:
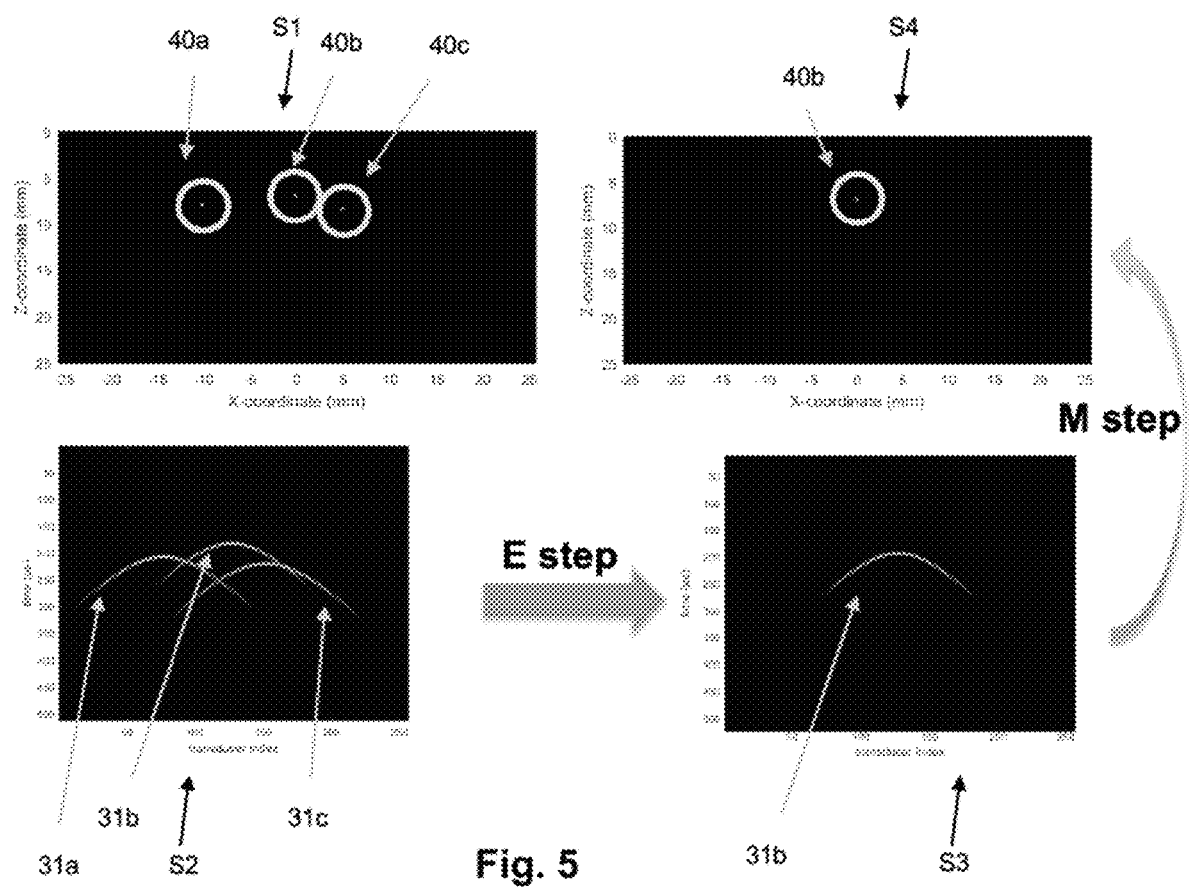
FIG. 5 shows the principles of a first example of a method for compensating clutter.

FIG. 5 shows the principles of a first example of a method for compensating clutter. In particular, FIG. 5 shows four stages of an exemplary Expectation-Maximization (E-M) method for compensating clutter. The used E-M algorithm may enable to separate the not-tractable problem of likelihood maximization into parallel easy likelihood maximizations.

In stage 51 beamformed data are shown (obtained for example in operation (c) of the method of FIG. 1) which may comprise undesired clutter.

In stage S2 the beamformed data may be transformed back into RF signal data. Accordingly, the pixels of the beamformed data matrix may be back-projected to the RF data matrix, i.e. to inverse the beamforming process.

In stage S3, for a plurality of different spatial regions or for each spatial region of the medium, modified RF signal data may be built by removing the contribution of other (or all other) spatial regions. Said operation may be referred to as the E (estimation) step. In the example of FIG. 5, the contribution of the reflectors associated with pixels 40a, 40c, i.e. arches 31a, 31c are "removed".

In stage S4 the modified RF signal data is beamformed, to obtain the beamformed data of isolated pixel 40b. A regular DAS beamformer may be used in for this purpose. Said operation may also be referred to as the M (Mximisation) step.

The E-step and the M-step may be repeatedly performed in a plurality of iterations. As starting point in the first iteration the first E-step may use conventional beamformed data (cf. stage 51), and the subsequent E-step may be based on the beamformed data obtained in the preceding M-step (cf. stage S4).

Every iteration of the method may result in a modified RF data matrix building step (cf. stage S3), based on the current image estimate followed by a regular DAS beamforming (cf. stage S4) operated on the modified RF data matrix.

The method of FIG. 5 may decouple the complicated multiparameter optimization problem of image beamforming while taking into account off-axis signals into N separate maximum likelihood optimizations, with N being the total number of spatial regions. However, the method of FIG. 5 iterates back and forth between beamformed data (i.e. parameter estimates) and RF signal data (i.e. observed data), which is computationally expensive.

Figure 6:
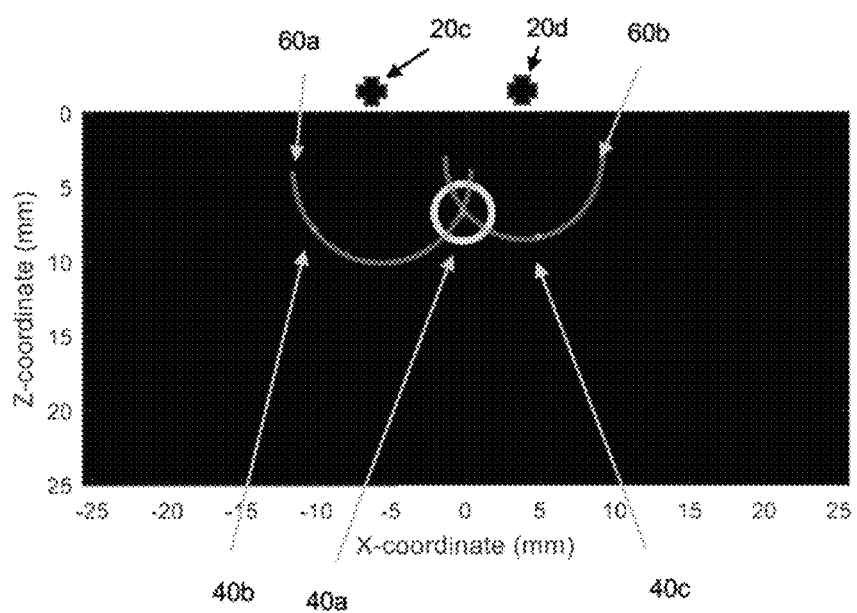
FIG. 6 shows the principles of a second enhanced exemplary embodiment of a method for compensating clutter according to the present disclosure.

FIG. 6 shows the principles of a second enhanced exemplary embodiment of a method for compensating clutter according to the present disclosure.

In the embodiment of FIG. 6 the method does not need to iterate back and forth between beamformed data (i.e. parameter estimates) and RF signal data (i.e. observed data) and can therefore be computationally less expensive (for example in view of the required time, resources, memory, power, etc.). In particular, the method may process merely beamformed data, i.e. operate merely with beamformed data.

It is possible to avoid iterating back and forth between beamformed data and RF signal data, since beamforming is a linear process. Therefore, removing a linear combination of signals from beamformed data is equivalent to removing a specific signal from RF data. Moreover, for predetermined or known characteristics of a transducer device (e.g. the geometry of the transducer array, the type of wave etc.) it is possible to predict which reflectors are going to impact a specific pixel, or in general terms, which second special region can cause clutter in a first set of beamformed data associated with a first region.

The improvement of the embodiment of FIG. 6 may consist in implementing the E-M method of FIG. 5 on beamformed data. The E step may remove a linear combination of second spatial regions (for example pixels) that are located so that they can generate clutter on a first spatial region (for example a pixel of interest). Accordingly, the M step is combined with the E step such that the computationally expensive back and forth processing of beamforming and inverse beamforming can be avoided.

Accordingly, the embodiment of FIG. 6 may save a significant amount of computation operations because it implies no need to back-project the pixels from the image to the RF data matrix, i.e. to inverse the beamforming process.

FIG. 6 schematically illustrates two transducer elements 20c, 20d and respective isochronous reception areas (schematically indicated by exemplary parabolas 60a, 60b). As further shown, pixel 40a associated with a respective region in the medium lies on parabola 60a, pixel 40c associated with a respective region in the medium lies on parabola 60b, and pixel 40b associated with a respective region in the medium lies on the overlapping section of parabolas 60a and 60b. The principles of estimating clutter may correspond to those described above in context of FIG. 2. However, in context of FIG. 6 it is referred to the beamformed data, i.e. to a first and a second set of beamformed data according to the present disclosure. In the example of FIG. 6, these first and second sets may be respective pixel 40a, 40b The signal data received from for example a first region associated with the first pixel 40a may be isochronous to signal data received from a second region associated with the second pixel 40b. Hence, since the signals associated with the respective first and second beamformed pixel may have the same propagation time at the transducer element 20c, the signals associated with the second pixel may cause clutter at the first beamformed pixel.

More generally, any pixel located on the parabola 60a may imply isochronous signal data for the (selected) first pixel 40a. Hence, these pixels may be determined as being associated with second spatial regions of the medium that are located such that they can cause clutter at the first pixel 40a.

For each of these pixels the clutter contribution may be estimated as a function of the amplitude or intensity of the determined pixels on the parabola 60a.

In a further option, in order to reduce computational power, only such pixels located on the parabola 60a may be considered for estimating the clutter, whose amplitude exceeds a predefined threshold. This may simplify the method and advantageously reduce computational costs.

Furthermore, in order to reduce further the clutter, the compensation method may be carried out in a plurality of iterations.

Instead of single pixels also groups or clusters of pixels may be considered as a set of beamformed data in the method.

A corresponding exemplary scenario is shown for transducer element 20d in view of pixels 40a and 40c being located on a parabola 60b relevant for the transducer element 20d. Accordingly, for transducer element 20b the clutter caused by a third region associated with pixel 40c may be estimated at pixel 40a. In other words, in order to estimate the clutter at pixel 40a, a plurality of transducer elements 20c, 20d may be considered. Said plurality of transducer elements may comprise all transducer elements of the transducer device or only those transducer elements whose signal data are used for determining pixel 40a (cf. also the iteration over loop L2, as explained above).

The embodiment of FIG. 6 may correspond to the method described in context of FIGS. 1 and 2 and may comprise any of the features described in the context of FIGS. 1 and 2.

The second spatial regions may also be determined according to the following example. In said example, a medium is insonified by means of a linear array that generates successive plane waves with varying incident angle. Furthermore, the response sequence of the medium received by the linear transducer array is processed to obtain two-dimensional beamformed data. In other words, the beamformed may be in the form of pixels in two-dimensional matrix. Each pixel may correspond to a set of beamformed data according to present disclosure (for example an in-phase and a quadrature phase, IQ, value).

$M(x_0, z_0)$ may be a first spatial region associated with a first beamformed IQ data set according to the present disclosure. $M(x_0, z_0)$ then refer to the pixel associated to this first spatial region. Then, the location of the second spatial regions that may cause clutter at the first. $N(x, z)$ refer to such second spatial regions. By construction, N and M share the same propagation time for a given transmitted angled plane wave $\theta_{in}$ and a given receive transducer element $P_{out}(x_{out}, z_{out}=0)$. In the following, the medium speed of sound is assumed constant and equal to c. The following demonstration aims at computed the coordinates (x, z) of point N that validate the above conditions.

The transmit propagation time $t_{in}$ required for the plane wave of angle $\theta_{in}$ to reach the point $M(x_0, z_0)$ can be expressed as, cf. equation (3):

$$t_{in}(\theta_{in}, x, z) = \frac{1}{c}(x_0 \sin(\theta_{in}) + z_0 \cos(\theta_{in})), \quad (3)$$

The receive propagation time $t_{out}$ required for echoes generated at point $M(x_0, z_0)$ to reach the transducer $P(u_{out}, 0)$ can be expressed as, cf. equation (4):

$$t_{out}(x_{out}, x, z) = \frac{1}{c}\sqrt{(x_0 - x_{out})^2 + z_0^2}. \quad (4)$$

The round-trip time of flight $t_0$ of echoes generated at point $M(x_0, z_0)$ and measured by transducer $P_{out}(x_{out}, z_{out}=0)$ can then be expressed as, cf. equation (5):

$$t(x_0, y_0, \theta_{in}, x_{out}) = \frac{1}{c}\left(x_0 \sin(\theta_{in}) + z_0 \cos(\theta_{in}) + \sqrt{(x_0 - x_{out})^2 + z_0^2}\right) = t_0. \quad (5)$$

By definition, $N(x, z)$ generates clutter at the pixel $M(x_0, z_0)$. Consequently, M and N are isochronous, meaning that they share the same round-trip propagation time for the given plane wave $\theta_{in}$ and received transducer $P_{out}$. As a result, the coordinates (x, z) are solution of the following equation (6):

$$t(x, z, \theta_{in}, x_{out}) = \frac{1}{c}\left(x \sin(\theta_{in}) + z \cos(\theta_{in}) + \sqrt{(x - x_{out})^2 + z^2}\right) = t_0. \quad (6)$$

After development, (Eq. (6)) can be expressed as, cf. equation (7):

$$x^2(1-\sin^2(\theta_{in})) + z^2(1-\cos^2(\theta_{in})) + 2 \times (ct_0 \sin(\theta_{in}) - x_{out}) + 2zct_0 \cos(\theta_{in}) -$$

$$2xz \cos(\theta_{in})\sin(\theta_{in}) + x_{out}^2 - c^2 t_0^2 = 0 \quad (7).$$

This equation corresponds to a quadratic curve. One may compute the determinant of the matrix of the quadratic J is null, cf. equation (8):

$$J = (1-\sin^2(\theta_{in}))(1-\cos^2(\theta_{in})) - (-\cos(\theta_{in})\sin(\theta_{in}))^2 = 0. \quad (8).$$

This characteristic ensure that the quadratic curve is a parabola.

In a first exemplary case, where the angle $\theta_{in}$ of the plane wave is zero, (Eq. (7)) can be simplified and the z coordinate of the second region may be determined as a function the x coordinate through the following equation (9):

$$z = \frac{-x^2 + 2xx_{out} - x_{out}^2 + c^2 t_0^2}{2ct_0}. \quad (9)$$

This equation corresponds to a parabola curve. Only point N(x, z) whose coordinates validate the above equation (9) should be considered as potential source of clutter at the first data set corresponding to the spatial region $M(x_0, z_0)$.

In a second exemplary case, the general problem may be considered. First a change of coordinates may be performed. The coordinate system may be rotated by an angle $\theta$ and a new coordinate system (x', z') may be obtained which can be described by, cf. equation (10) and (11):

$$x = x' \cos(\theta) + z' \sin(\theta) \quad (10)$$

$$z = -x' \sin(\theta) + z' \cos(\theta) \quad (11)$$

By using these new coordinates, (Eq. 7) can be simplified and z' can be expressed as a function of x', cf. equation (12):

$$z'_{cl} = \frac{x'^2(\cos^4(\theta) + \sin^4(\theta)) - 2x'^{x_{out}}\cos(\theta) + x_{out}^2 - c^2 t_0^2}{2\sin(\theta)x_{out} - ct_0} \quad (12)$$

Once x' and z' have been determined, it may be reverted to x and z if necessary, by a rotation of the angle $-\theta$.

Throughout the description, including the claims, the term "comprising a" should be understood as being synonymous with "comprising at least one" unless otherwise stated. In addition, any range set forth in the description, including the claims should be understood as including its end value(s) unless otherwise stated. Specific values for described elements should be understood to be within accepted manufacturing or industry tolerances known to one of skill in the art, and any use of the terms "substantially" and/or "approximately" and/or "generally" should be understood to mean falling within such accepted tolerances.

Although the present disclosure herein has been described with reference to particular embodiments, it is to be understood that these embodiments are merely illustrative of the principles and applications of the present disclosure.

It is intended that the specification and examples be considered as exemplary only, with a true scope of the disclosure being indicated by the following claims.

A reference herein to a patent document or any other matter identified as prior art, is not to be taken as an admission that the document or other matter was known or that the information it contains was part of the common general knowledge as at the priority date of any of the claims.

The invention claimed is:

1. A method for processing beamformed data of a medium, the method comprising:
   obtaining a first set of beamformed data associated with a first spatial regions; and
   obtaining a second set of beamformed data associated with a second spatial region, the second set of beamformed data being isochronous with the first set of beamformed data, and
   estimating clutter caused by the second spatial region at the first set.

2. The method according to claim 1, further comprising:
   selecting the first set and determining the second set as a function of the location of the associated second spatial region, wherein the second spatial region is located such that the first set is susceptible for clutter generated at the second spatial region, and/or
   selecting the second set and determining the first set as a function of the location of the associated first spatial region, wherein the first spatial region is located such that the first set is susceptible for clutter generated at the second spatial region, and/or
   compensating the estimated clutter at the first set, and/or removing the clutter at the first set.

3. The method according to claim 1, wherein at least one of:
   the clutter is estimated as a function of at least one of the location of the first spatial region and the location of the second spatial region,
   the clutter is estimated as a function of the second set and/or the amplitude of the second set, and
   the second set is considered for estimating the clutter, when the amplitude of the second set exceeds a predefined threshold.

4. The method according to claim 2, wherein:
   determining the second set of beamformed data comprises:
      determining a plurality of second sets of beamformed data respectively associated with a plurality of second spatial regions that are located such that the first set is susceptible for clutter generated at the second spatial regions, and estimating the clutter at the first set comprises:
      estimating a plurality of clutter contributions respectively associated to the second sets, the clutter at the first set being a function of the plurality of clutter contributions.

5. The method according to claim 1, wherein the clutter at the first spatial region is estimated by a linear combination of the plurality of clutter contributions at the first spatial region.

6. The method according to claim 1, further comprising before selecting at least one of the first and the second set:
   processing ultrasound signal data of the medium to obtain the beamformed data.

7. The method according to claim 1, further comprising before processing ultrasound signal data or selecting beamformed data:
   transmitting an emitted sequence of ultrasound waves into the medium, and
   receiving a response sequence of ultrasound waves from the medium, wherein the ultrasound signal data are based on the response sequence of ultrasound waves.

8. The method according to claim 1, wherein at least one of the first and second set is further determined and/or the clutter is further estimated as a function of at least one of:
   the geometry of a transducer device used for acquiring data of the medium on which the beamformed data are based,
   the arrangement and/or the size of the single transducer elements of the transducer device,
   at least one of the emission and receive aperture of the transducer device,
   the emission duration,
   the wavelength and/or type of emission pulse on which the beamformed data is based,
   the geometry of the emitted wave front, and
   a predetermined speed of sound model of the medium.

9. The method according to claim 1, wherein at least one of:
  each set of beamformed data is associated with at least one pixel or voxel and
  the beamformed data are in-phase and quadrature phase, IQ, data and/or radio frequency, RF, data.

10. Method according to claim 1, wherein
  at least one of the first set, the second set, the first spatial region and the second spatial region is predetermined.

11. The method according to claim 1, wherein the method is performed for a plurality of first spatial regions of the medium, in parallel and/or in series.

12. The method according to claim 1, wherein the method is performed for the first spatial region in several iterations, wherein at each iteration modified beamformed data is obtained by compensating the estimated clutter, wherein the modified beamformed data obtained in a first iteration is used in a subsequent second iteration.

13. A method of training an artificial intelligence-based model (AI) based on an estimated clutter according to the method of claim 1.

14. A method for processing beamformed data of a medium, the method comprising: using the AI based model of claim 13 to estimate an amount clutter and/or compensate an estimated clutter.

15. A computer program comprising computer-readable instructions which when executed by a data processing system cause the data processing system to carry out the method according to claim 1.

16. A system for processing beamformed data of a medium, the system comprising a processor and a memory, the beamformed data comprising a first set of beamformed data associated with a first spatial region and a second set of beamformed data associated with a second spatial region, wherein the processor is configured to:
  determine the first set of beamformed data;
  determine the second set of beamformed data, the second set of beamformed data being isochronous with the first set of beamformed data; and
  estimate the clutter caused by the second spatial region at the first set based on the determined first set of beamformed data and second set of beamformed data.

* * * * *